United States Patent [19]

Neal

[11] Patent Number: 5,000,195
[45] Date of Patent: Mar. 19, 1991

[54] ANKLE SPLINT

[75] Inventor: Charles O. Neal, Knoxville, Tenn.

[73] Assignee: DeRoyal Industries, Inc., Powell, Tenn.

[21] Appl. No.: 209,521

[22] Filed: Jun. 21, 1988

[51] Int. Cl.$^5$ ............................ A61F 3/00; A61F 5/04; A61F 13/06

[52] U.S. Cl. ................................ 128/80 H; 128/87 R; 128/166

[58] Field of Search ................. 128/87 R, 87 C, 89 R, 128/87 A, 165, 166, 80 H

[56] References Cited

U.S. PATENT DOCUMENTS

| | | | |
|---|---|---|---|
| 672,146 | 4/1901 | Collis | 128/166 UX |
| 1,090,906 | 3/1914 | Collis | 128/166 UX |
| 1,231,332 | 6/1917 | Collis | 128/166 |
| 2,774,152 | 12/1956 | Alber | 36/71 |
| 2,830,585 | 4/1958 | Weiss | 128/166 |
| 3,298,365 | 1/1967 | Lewis | 128/80 |
| 3,506,000 | 4/1970 | Baker | 128/166 |
| 3,515,136 | 6/1970 | Baker | 128/166 |
| 3,970,083 | 7/1976 | Carrigan | 128/166 |
| 4,187,844 | 2/1980 | Caprio, Jr. | 128/166 |
| 4,237,874 | 12/1980 | Nelson | 128/80 |
| 4,280,488 | 7/1981 | Polsky et al. | 128/166 |
| 4,313,433 | 2/1982 | Cramer | 128/166 X |
| 4,323,058 | 4/1982 | Detty | 128/166 X |
| 4,440,158 | 4/1984 | Shapiro | 128/166 X |
| 4,527,556 | 7/1985 | Nelson | 128/80 |
| 4,590,932 | 5/1986 | Wilkerson | 128/166 |
| 4,638,794 | 1/1987 | Grisar | 128/80 |
| 4,719,926 | 1/1988 | Nelson | 128/80 |
| 4,727,863 | 3/1988 | Nelson | 128/166 X |
| 4,729,370 | 3/1988 | Kallassy | 128/166 |

Primary Examiner—Robert A. Hafer
Assistant Examiner—Michael Brown
Attorney, Agent, or Firm—Luedeka, Hodges, Neely & Graham

[57] ABSTRACT

An orthopedic ankle splint including an elongate body panel adapted to underlie the arch of the foot and extend upwardly from the arch to overlie the medial and lateral sides of the ankle. The posterior side edges of the panel are joined as by an elastic member and the anterior side edges of the panel are joined as by lacing. The central portion of the body panel is cut away to provide a heel opening and to provide for an upward pull on the arch of the foot toward dorsiflexion when the splint is laced to the ankle. Optionally, the splint includes a strap which is releasably anchored at one of its ends to one side of the arch area, extends beneath the arch, upwardly along the lateral side of the foot, overwrapping the superior surface of the ankle, and has its other end releasably anchored to the exterior surface of the splint at a location immediately above the medial malleolus. Such strap provides for support to and restraint against inward and downward flexion or hyperextension of the ankle, especially the anterior talofibular ligament.

3 Claims, 3 Drawing Sheets

ANKLE SPLINT

FIELD OF THE INVENTION

This invention relates to orthopedic medical devices of the type intended to be applied to the ankle and underlie the arch of the foot and extend upwardly from the arch along and wrapping opposite sides of the ankle to provide both support and compression to the ankle.

BACKGROUND OF THE INVENTION

Ankle injuries commonly are of a sprain variety and the present invention is specially designed to serve as an aid in the treatment of sprains. Sprains are the tearing or stretching of a ligament. Ligaments connect bone to bone and serve to stabilize the joint, thus it is a primary function of an ankle splint to aid in the support of the joint during the natural healing process of recovering from a sprain. Sprains are classed in three degrees. A grade one sprain is a partial tear without any loss of integrity of the joint. A grade two sprain is a more extensive tear, yet the ligament is still intact. A grade three sprain is a complete tear which compromises the integrity of the joint.

Tendons connect muscles to bones. A strain is a stretching or tearing of a muscle and/or the covering of the muscle, usually without serious damage to the tendons. Inasmuch as body joints are held together by the combined action of ligaments and tendons (with the interconnecting muscles), ankle splints are intended to also provide a measure of joint integrity in the event of a strain as well as in the event of a sprain.

The most common mode of ankle injury is a sudden inversion injury with a lateral tear. The anterior talofibular ligament usually tears first. A common scenario is for a patient to appear at an emergency room or doctor's office with a history of a forced inversion injury of the foot in plantar flexion (a down and in type of injury). The ankle is swollen, painful and tender. There is usually a large area of ecchymosis, comprising hemorrhagic areas under the skin with blood under the fascia and and often extending completely to the bottom of the foot.

The treatment of choice for most ankle strains or sprains is rest (removal of body support pressure from the ankle), application of ice or other cooling medium to the ankle for the first 48 hours following injury, elevation of the injured ankle until the swelling has subsided, and compression applied to the ankle to compliment venous return and to reduce swelling and congestion. During the recovery period following a sprain in particular, especially where the sprain is of the second or third degree, it is important that the ankle be maintained in its neutral, i.e. natural, position of alignment with the leg so that the injured members are not allowed to redevelop out of position, or to foreshorten, etc.

It is an object of the present invention to provide an ankle splint useful in providing support and compression to an ankle, especially in the course of treatment of a strain or sprain of the ankle.

It is another object of the present invention to provide an ankle splint which maintains the foot, hence the ankle in its natural orientation during the recovery from an injury of the ankle.

It is another object of the present invention to provide an ankle splint having multiple features for supplying support and/or compression to the ankle.

It is another object of the present invention to provide an ankle splint wherein the compression support to the ankle is primarily applied to the soft tissues of the ankle.

Other objects and advantages of the invention will be recognized from the description contained herein including the drawings in which.

Figure 1:
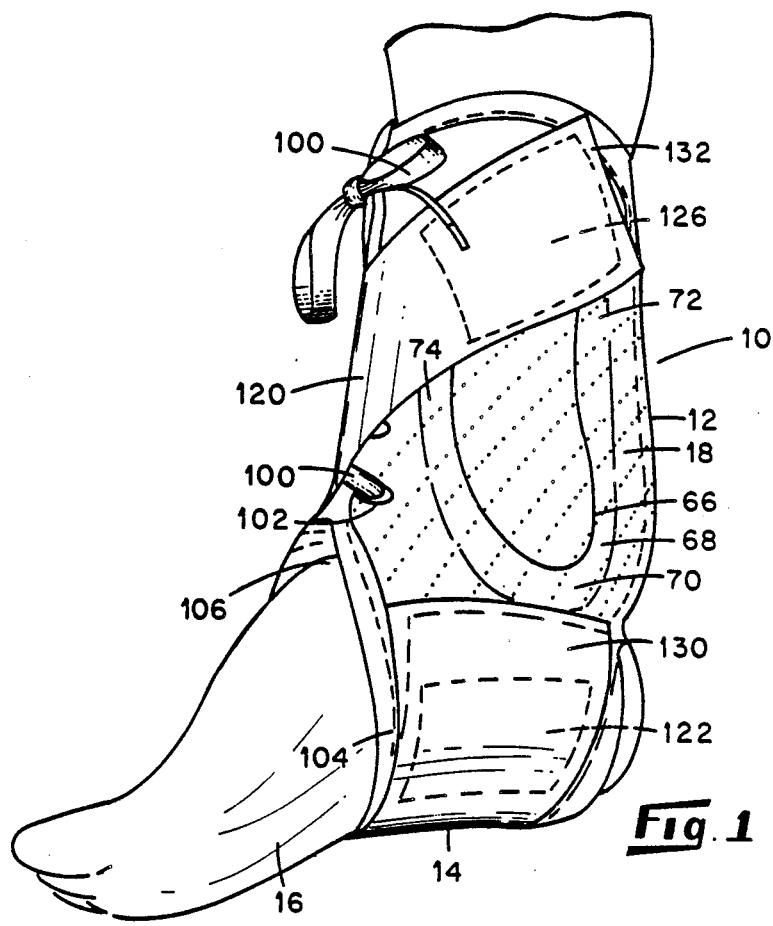
FIG. 1 is a representation of one embodiment of the present ankle splint as applied to an ankle.

In accordance with the present invention there is provided an improved ankle splint comprising an elongate body panel adapted to underlie the arch of the foot and extend upwardly from the arch to overlie the medial and lateral sides of the ankle thereby positioning portions of the side edges of the body panel in facing relationship on the posterior and on the anterior sides of the ankle when the panel is on the ankle. The posterior and anterior side edges of the body panel are cut away in its central region. An elongated elastic panel joins those portions of the facing posterior side edges of the body panel that overlie the ankle, while the facing anterior side edges of the body panel are joinable as by lacing. By reason of the cooperating geometries of the several elements of the present splint, when the splint is fitted to the ankle, the plane of the bottom of the foot is positioned and maintained at an angle of between about 84 degrees and 96 degrees with respect to the longitudinal axis 110 of the lower leg, thereby maintaining the ankle bones, muscles and ligaments in their neutral and natural respective positions of alignment, while simultaneously supplying compression to the ankle, particularly in the areas surrounding the lateral and medial malleolus and containing the anterior talofibular ligament. In one embodiment, a strap means is releasably anchored at one of its ends on one side of the arch area, extends therefrom beneath the arch, upwardly along the lateral side of the foot, overwrapping the superior surface of the ankle, and has its other end releasably anchored to the exterior surface of the splint at a location immediately above the medial malleolus, thereby providing support to and restraint against inward and downward flexion or hyperextension of the ankle, especially the anterior talofibular ligament.

With reference to the several FIGURES, in a preferred embodiment, the present ankle splint 10 includes, an elongated major body panel 12 that is of sufficient length as permits its central region 14 to underlie the arch of the foot 16 and its opposite end panels 18 and 20 to extend upwardly and overlie the lateral and medial sides 22 and 24 of the ankle 26 to a location about 3 inches above the lateral malleolus and the medial malleolus.

Figure 5:
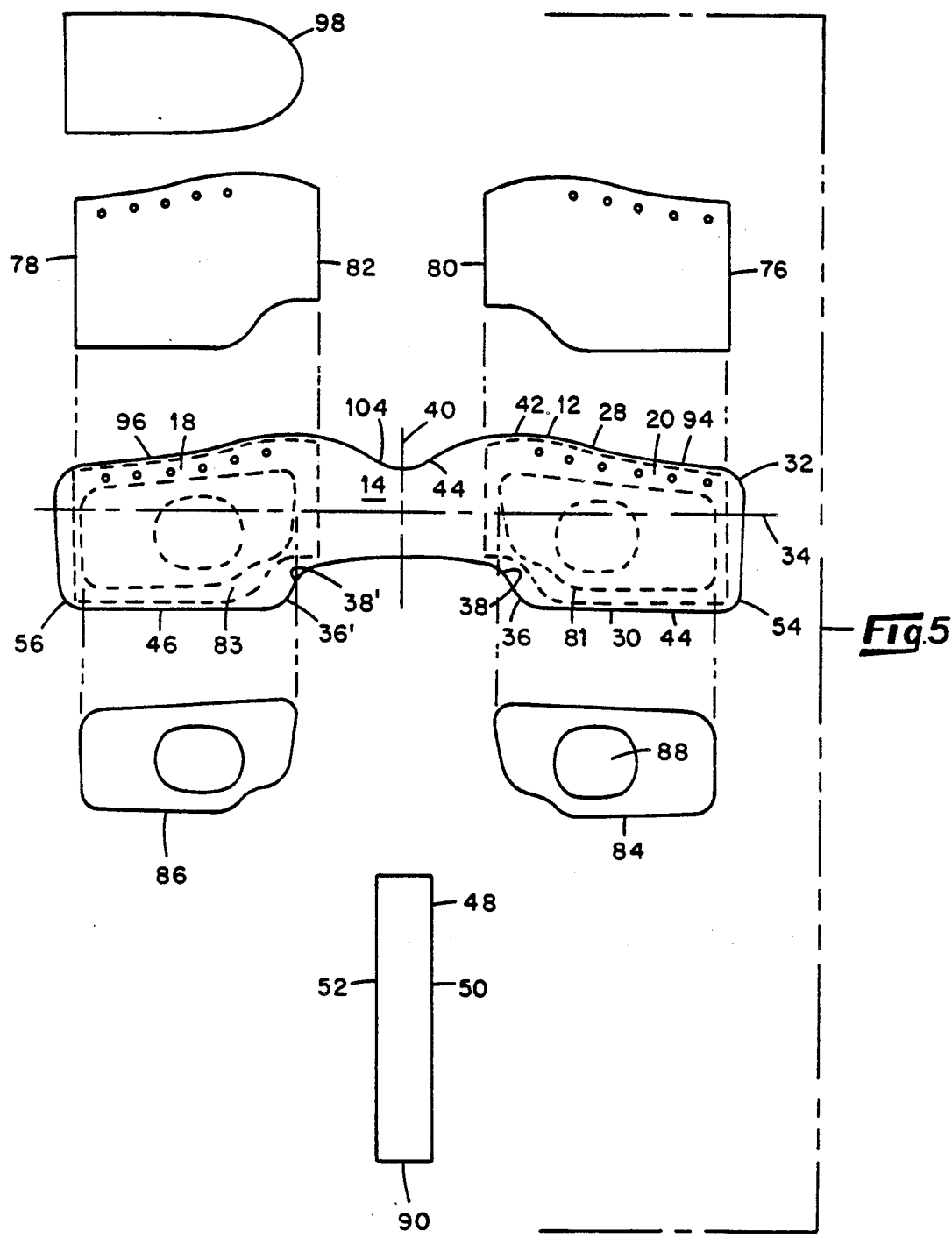
FIG. 5 is an exploded view depicting various individual components of one embodiment of the present ankle splint.

Referring specifically to FIG. 5, the depicted elongate body panel 12 is cut away in its central region 14 along both the anterior and posterior side edges 28 and 30, respectively, to reduce the width of body panel in such central region that underlies the arch of the foot when the splint is fitted on the ankle. It has been discovered that the depicted geometries, i.e. contours and extent, of the cutaways are important in developing the desired positioning of the foot, hence the bones and ligaments of the ankle, with respect to the longitudinal axis of the leg during the recuperative period following an ankle injury. When the body panel is viewed in a flat, laid out position as depicted in FIG. 5, it may be seen that the posterior side edge 30 of the body panel extends from one end 32 of the panel along a substantially straight line that is substantially parallel to the longitudinal axis 34 of the panel to a location where the side edge curves inwardly in a first curve 36 toward the longitudinal axis 34 for a distance equal to about ⅓ of the major width of the panel, and then again curves in a second curve 38 oppositely to the first curve 36 to continue in a direction substantially parallel to the longitudinal axis, to the transverse axis 40 of the panel.

The anterior side edge 28 of the panel extends from the panel end 32 along a path that angles away from the longitudinal axis of the panel by a relatively slight angle, e.g. between about 5 degrees and 15 degrees, for a distance equal to about two-thirds of the distance between the end 32 and the transverse axis 40 of the panel. At this location 42, the side edge 28 begins a smooth curvilinear transition toward the longitudinal axis, such transition reversing itself at 44 a slight distance prior to the transverse axis 40 of the panel. The body panel is symmetrical about its transverse axis so that the opposite end panels 18 and 20 of the body panel are mirror images of one another so that their side edges are likewise mirror images.

When the body panel is folded along its transverse axis, the posterior side edges 44 and 46 of the end panels 18 and 20 are juxtapositioned. An elongated, preferably rectangular, elastic strip 48 is disposed between such side edges and secured along its side edges 50 and 52 to the side edges 44 and 46 of the body panel, thereby joining such side edges 44 and 46. As depicted, the elastic strip is of substantially uniform width and extends from the ends 54 and 56 of the side edges to a location past the first curves 36 and 36, of the posterior side edges and terminates short of the second curves 38 and 38'. As depicted in the FIGURES, and specifically in FIG. 5, the central region 14 of the body panel 12 is of a width less than the width of the end panels 18 and 20 and, by reason of the geometry of the central region, within the central region 12 the unsecured length of the posterior side edge 104 is of a length greater than the unsecured length of the anterior side edge of such central region.

Figure 2:
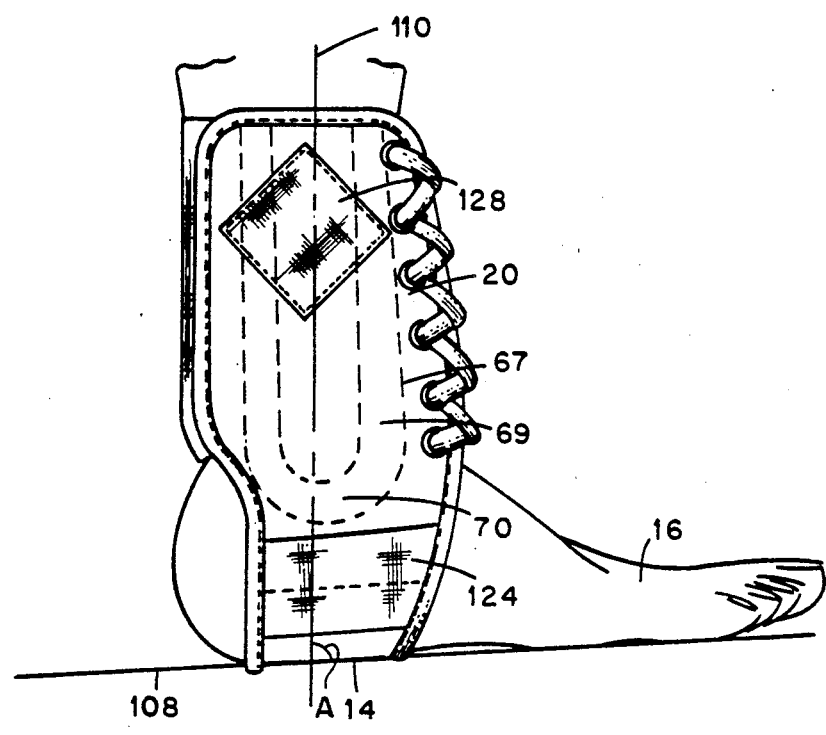
FIG. 2 is a schematic representation of one embodiment of the present ankle splint as applied to an ankle and viewed from the lateral side, showing the foot as held in the neutral position by the depicted splint.
Figure 3:
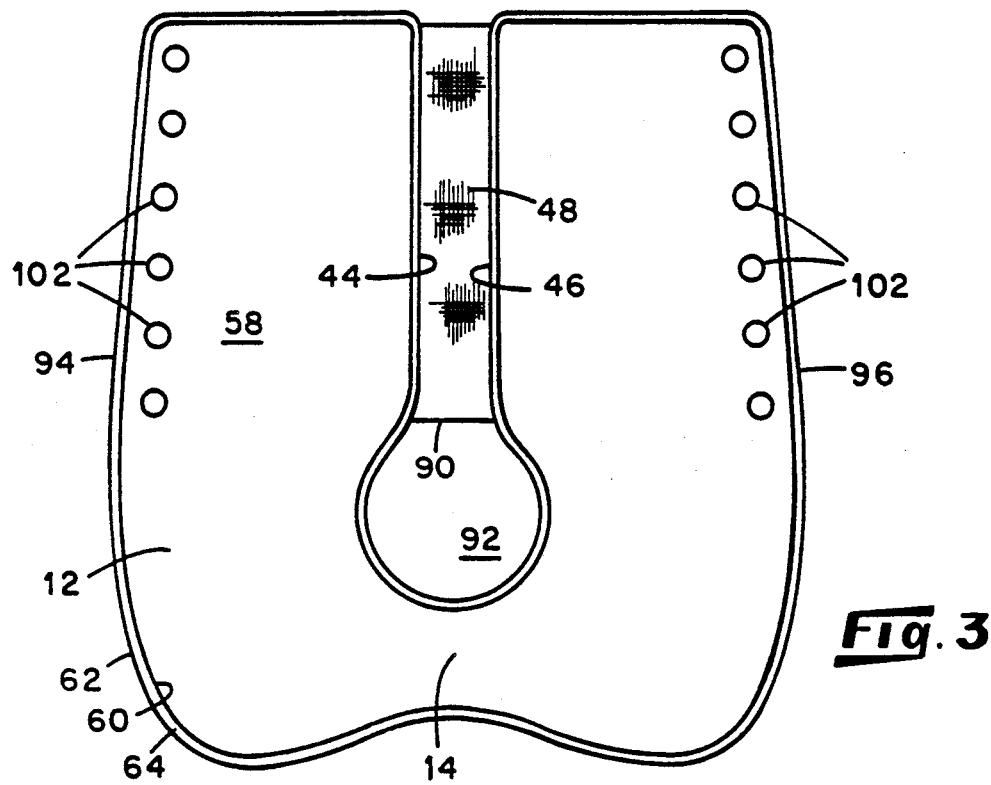
FIG. 3 is a representation of one embodiment of the principal body member of the present ankle splint.
Figure 4:
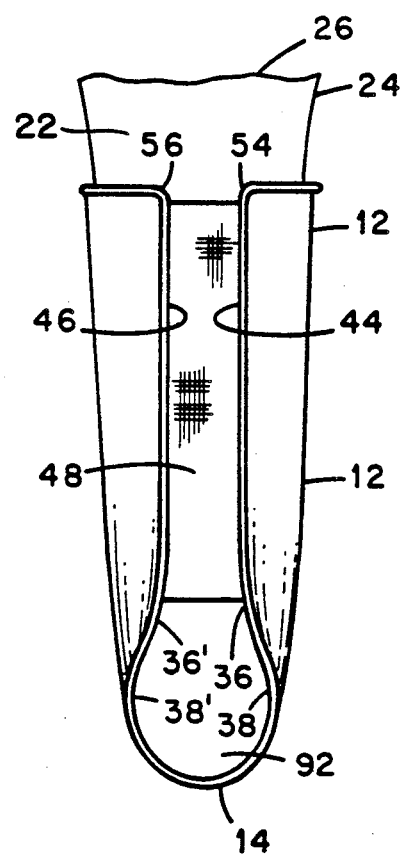
FIG. 4 is a rear elevational view of the body member depicted in FIG. 3 and when applied to an ankle.

On that surface of the body panel which faces the ankle when the splint is fitted on the ankle, in one embodiment there is provided a liner 58 that is of the same geometry as the body panel 12. This liner is joined along its perimeter 60 to the perimeter 62 of the body panel as by stitching. In the preferred embodiment, the joined perimeters are covered as by a binding 64. In one embodiment, the liner 58 and body panel 12 are further joined by stitching to define a U-shaped pocket 66 and 67 (see FIGS. 1 and 2) between the liner and body member in each end panel 18 and 20 to receive therein a U-shaped stay 68 and 69, respectively. As shown in the FIGURES, the bend 70 of the stay 66, for example, is disposed below the malleolus and the legs 72 and 74 of the stay extend upwardly along opposite sides of the malleolus.

Additionally, as best seen in the embodiment depicted in FIG. 5, the end panels 18 and 20 are each provided with a further panel 76 and 78, respectively, which is joined about their respective perimeters, except along their top edges 80 and 82, to the respective end panels and on the inwardly facing surface of each such end panel, thereby defining further pockets 81 and 83 for receiving one or more planar stays 84 and 86. The positions of the pockets 81 and 83 on the body panel are such as causes them to overlie the malleolus. Accordingly, each of the stays deployed in such pockets are provided with an aperture 88 of a size and location such that when the stay is disposed in its pocket, the aperture receives the malleolus and those portions of the stay surrounding the aperature supply support and compression to the soft tissue around and adjacent to the malleolus.

In one embodiment, the body panel of the present ankle splint is fabricated of a vinyl material that is readily conformable to the ankle and sufficiently non-yielding to permit development of the desired support for the ankle. A liner of sateen or similar cloth material provides good strength enhancement to the body panel and presents a smooth surface facing the ankle, especially in the area of the arch.

Preferably, the vinyl body panel and the liner 58 are perforated to promote air flow through their thickness dimension. Therefore, the liner, if not also perforated, should be of a relatively air permeable material to permit the desired air flow. Joinder of the liner to the body panel about their congruent perimeters preferably is accomplished by stitching a cotton or polyester binding to the perimeters. For forming the stay pockets 81 and 83, each the panels 76 and 78 preferably is a layered composite including a central layer of soft foam that is faced on one surface with a layer of cotton or nylon tricot and faced on its opposite surface with a brushed or napped cotton or polyester cloth. This latter surface faces the ankle to provide a soft, cushiony feel to the ankle, while the foam composite helps in reducing the tendency of the edges of aperture 88 from tending to gouge into the ankle when the splint is applied.

The elastic strip 48 which joins the upper portions of the posterior side edges 44 and 46 of the end panels is about 1½ inches wide and 6 inches long in one embodiment, i.e. "small" size. The elastic preferably is stitched to the side edges using a blindstitch machine to provide strong and relatively smooth stitching. The spacing between the side edges, after the elastic strip is sewn in, is less than the width of the ankle, e.g. about 1 inch. Importantly, the lowermost end 90 of the elastic strip is stretched as it is sewn to cause it to follow the curvature of the side edges 44 and 46 so that in such curved region of the side edges, the width between the side edges increases gradually from the point on the side edge where the curvature commences, to a point about halfway between the first and second curves 36 and 38, and 36' and 38' referred to hereinabove. By this means, there is defined the top edge of a heel opening 92 in the splint that readily receives and conforms to the full heel while preventing inordinate pressure against the Achilles tendon when the splint is fitted snugly on the ankle. Extension of the elastic strip fully up the posterior of the splint serves to impart to the splint a desirable degree of resiliency as regards the tightness of the fit of the splint on the ankle to avoid constricting the flow of blood into the ankle area, thereby promoting healing, and to provide a measure of protection to the Achilles tendon as it extends up the posterior side of the ankle while permitting a limited degree of normal flexion of the ankle. Such limited flexion motion is at times desirable and beneficial in keeping the ankle supple during recuperation from a sprain or strain of the inversion type.

When the present splint is in position on the ankle, the anterior side edges 94 and 96 of the body panel are disposed along the anterior surface of the ankle, these edges being juxtaposed and facing one another. Preferably, a tongue 98 of the same material as the body panel, is disposed between these anterior side edges and the ankle. Lacing 100 is threaded through a plurality of eyelets 102 secured along the side edges 94 and 96 provides for adjustably drawing the side edges toward one another to pull the splint snug against and in conformity with the ankle. Other relatively nonyielding, releasable closure means may be employed, such as Velcro closures.

Importantly, by reason of the cutaway from the central anterior side edge of the body panel, such central side edge wraps beneath the arch of the foot at a location beginning substantially centrally of the instep as opposed to a wrapping location nearer the ball of the foot. By this means, when the lacing is drawn, the anterior side edges of the body panel are pulled toward one another. By reason of the cutaway geometry of the body panel described hereinabove, when the splint is in place on the ankle, the anterior side edge 104 of the central region of the body panel extends from the superior surface 106 of the arch downwardly and rearwardly along the opposite sides of the ankle toward the arch. Thus, when the lacing is pulled taut, there is produced an upward and forwardly pull on the anterior side edge 104 which tends to foreshorten such side edge and rotate the foot in dorsiflexion thereby urging the toe portion of the foot upwardly. The extent of such dorsiflexion is limited by the geometry of the body panel and is selected so as to maintain the plane 108 of the bottom of the foot 16 at an angle of between about 84 degrees and 96 degrees with respect to the longitudinal axis 110 of the leg (see FIG. 2). In the absence of such angular positioning of the ankle during recuperation from a sprain, especially a grade two or three sprain, there is a tendency for the ligaments to foreshorten with resultant loss in the degree of mobility of the ankle, especially in flexion.

The present ankle splint preferably is sized, e.g. pediatric, small, medium, large, or x-large so that the applying physician or therapist can select that size which causes the anterior side edges of the body panel to be juxtaposed, i.e. adjacent but spaced apart from one another along the approximate midline of the superior surface of the foot. Thus, the lacing may be employed to pull these side edges toward one another and exert the aforedescribed upward pull upon the arch to urge the foot toward its neutral position. Accordingly, the degree of rotation within the preferred range is selectable in part by the tautness of the lacing when the proper size splint is used.

Once the present splint is laced in position on the foot, a strap 120 of a conformable nonyieldable material about 2 inches in width may be applied to provide supplementary support to and restraint against inward and downward flexion or hyperextension of the ankle, especially the anterior talofibular ligament. The depicted strap 120 is of a looped pile fabric that is suitable as the loop element of a hook and loop (e.g. Velcro) type releasable fastener. The body panel 12 has fixedly secured thereto hook elements 122 and 124 of such fastener type at locations on lateral and medial outer surfaces of the body panel within the central region of the body panel so that when the splint is fitted on the foot, such hook elements are disposed on opposite sides of the foot immediately above the bottom of the foot in the arch. Similar hook elements 126 and 128 are fixedly secured to the outer surface of the body panel at respective locations on the lateral and medial sides of the body panel and near to uppermost ends of the end panels 18 and 20 when the splint is fitted on the foot. In application, one end 130 of the strap 120 is releasably secured to the hook element 122 on the medial side of the splint, passed under the arch, thence upwardly and forwardly to overlie the lateral side of the ankle, to wrap the superior surface of the ankle, and have its opposite end 132 releasably secured to the hook element 126. In this manner, the strap secures the foot and ankle against the undesired down and in motion that especially causes damage to the anterior talofibular ligament.

The present splint is notably universal as concerns use on the left or right ankle. This is provided for in part by forming the body panel symmetrically and by providing hook elements on both the medial and lateral sides of the splint to permit the strap 120 to be applied as described.

What is claimed:

1. A splinting device for an ankle providing enhanced angular alignment of the ankle with respect to the leg and compression to minimize swelling following a strain or sprain comprising:

an elongated substantially nonyielding flat body panel including first and second end panels cojoined by a central region, said central region adapted to underlie the arch of the foot when the splint is applied thereto, with said end panels adapted to extend upwardly along opposite sides of the ankle and overlying the ankle upwardly from the arch and at least past the lateral and medial malleolus thereby positioning the posterior side edges of said end panels in separated, but juxtaposed, relationship along the posterior side of the ankle, and the anterior side edges of said end panels in separated, but juxtaposed relationship along the anterior side of the ankle;

said central region being of reduced width relative to said end panels and being formed by an arcuate recession along the central anterior side edge of said body panel and by a cutaway along the central posterior side edges of said body panel, whereby said arcuate recession of anterior side edge extends from the superior surface of the instep of the ankle downwardly and rearwardly along opposite sides of the ankle to underlie the arch of the foot in position to exert a dorsiflexion force against the ankle as the anterior side edges of said end panels are drawn toward one another;

resilient means joining said first and second end panels along their respective posterior side edges from the uppermost ends thereof to a location approximately adjacent the stepped cutaway thereof and;

relatively nonyielding means releasably and adjustably joining said first and second end panels along their respective juxtaposed side edges from the uppermost ends thereof to the approximate midpoint of the instep.

2. An ankle splint of the type adapted to engage the foot and ankle of a patient and provide support, at least partial immobilization, and compression comprising:

an elongated substantially nonyielding and substantially flat body panel having a longitudinal axis and a central transverse axis and including:

first and second end panels and a central region;

said central region being adapted to underlie the arch of the foot, and said end panels being adapted to overlie the lateral and medial surfaces of the ankle when said splint is positioned on the ankle;

said body panel having anterior and posterior side edges;

when said body panel is laid out flat, said posterior side edge of said body panel extending substantially parallel to said longitudinal axis of said body panel from the opposite ends of said body panel toward the transverse axis thereof for a distance approximately one-third of the length of said body panel from the respective opposite ends thereof, said posterior side edge along one end panel curving from a substantially straight line inwardly of said body panel toward the longitudinal axis thereof a distance of less than about 30% of the width of said end panel at the juncture of said end panel with said central region, thence extending along a slightly arcuate path along the longitudinal axis of said central region toward the opposite one of said end panels, and at the approximate juncture of said central region with said opposite one of said end panels, curving away from said longitudinal axis to said posterior side edge of said opposite one of said end panels, whereby when said end panels are disposed along the lateral and medial surfaces of the ankle, said posterior side edge of said central region defines an opening for receiving a heel therein;

said anterior side edge of said body member extending from one end of said body member toward the transverse axis of said body panel along a generally straight line that forms an acute angle with a longitudinal axis of said body panel to the approximate location of the juncture of said end panel with said central region, and then along an arcuate path inwardly toward the longitudinal axis of said body panel and said transverse axis of said body panel, and then along a path from the transverse axis of said body panel to the opposite end of said body panel that is a mirror image of the path of said side edge on the opposite side of said transverse axis, whereby when said end panels are disposed along the lateral and medial surfaces of the ankle, said anterior side edge of said central region defines an opening for the instep region of the foot;

means connecting said posterior side edges of said end panels to one another when said end panels overlie said lateral and medial sides of said ankle;

means releasably and adjustably connecting said anterior side edges of said end panels to one another when said end panels overlie said lateral and medial sides of said ankle;

when connected, said posterior side edges being separated by a distance less than the distance of separation of said anterior side edges, thereby effectively foreshortening the length of said anterior side edge of said medial panel relative to the length of said posterior side edge of said medial panel to urge the anterior side edge of said medial panel toward the instep and thereby urge the foot forward to a neutral flexion position.

3. A body member for an ankle splint of the type adapted to engage the ankle and foot and provide support and compression for the ankle comprising:

a conformable elongated substantially nonyielding flat fabric having a longitudinal dimension, transverse axis, and opposite end sections, said fabric being substantially symmetrical about said transverse axis, such that the opposite end sections of said fabric form substantially mirror images of one another;

each of said end sections being of a width sufficient to cover less than all of one side of said ankle when positioned in overlying relationship to said ankle;

each of said end section shaving a posterior and an anterior side edge;

said posterior side edge extending from the outboard end of said fabric toward said transverse axis along a substantially straight path that is substantially parallel to said longitudinal axis to a location approximately two-thirds of the distance from said outboard end to said transverse axis, then curving inwardly towards said longitudinal axis, and thence along a slightly arcuate path to said transverse axis;

said anterior side edge extending from said outboard side end of said fabric toward said transverse axis along a substantially straight path that is angled acutely away from said longitudinal axis to a location approximately two-thirds of the distance from said outboard end to said transverse axis, then extending curvilinearly inwardly toward said longitudinal axis and said transverse axis to a location short of said transverse axis thence extending curvilinearly along a path that is substantially parallel to said longitudinal axis and which terminates at said transverse axis.

* * * * *